United States Patent [19]

Itoh et al.

[11] Patent Number: 4,534,980
[45] Date of Patent: Aug. 13, 1985

[54] ANTIINFLAMMATORY AND ANTIPYRETIC CREAM

[75] Inventors: Yasuo Itoh, Katsuyamashi; Hideo Kato, Fukuichi; Kugako Matsumura, Katsuyamashi; Tomoyasu Nishikawa, Oonoshi; Akira Hisano, Katsuyamashi; Takehisa Yamada, Katsuyamashi; Eiichi Koshinaka, Katsuyamashi, all of Japan

[73] Assignee: Hokuriku Pharmaceutical Co., Ltd., Katsuyamashi, Japan

[21] Appl. No.: 633,139

[22] Filed: Jul. 23, 1984

[30] Foreign Application Priority Data

Apr. 3, 1984 [JP] Japan ............................ 59-066228

[51] Int. Cl.$^3$ ............................................. A61K 31/19
[52] U.S. Cl. .................................... 514/570; 514/627; 514/871
[58] Field of Search ................................ 424/317, 324

[56] References Cited

U.S. PATENT DOCUMENTS 4,393,076 7/1983 Noda et al. .......................... 424/37
4,486,436 12/1984 Sunshine et al. .................... 424/317

FOREIGN PATENT DOCUMENTS 615137 1/1949 United Kingdom ............... 424/324

OTHER PUBLICATIONS

Chemical Abstracts, vol. 98, No. 24, Jun. 13, 1983, Abstract 98:204430y.
Chemical Abstracts, vol. 99, No. 8, Aug. 22, 1983, Abstract 99:58919s.
Chemical Abstracts, vol. 99, No. 14, Oct. 3, 1983, Abstract 99:110780f.
The Merck Index 10th Edition, published by Merck & Co., Inc., Rahway, N.J., 1983, p. 372, entry 2583.

*Primary Examiner*—Ronald W. Griffin
*Attorney, Agent, or Firm*—Gordon W. Hueschen

[57] ABSTRACT

Creams for external or topical use comprising ketoprofen as an effective component and crotamiton as an agent for preventing crystalline precipitation of the effective component. The creams possess an antiinflammatory and antipyretic effect and are excellent in permeation and absorption into the skin which enables the topical and external use of the creams.

2 Claims, No Drawings

ANTIINFLAMMATORY AND ANTIPYRETIC CREAM

BACKGROUND OF THE INVENTION

1. Field of the Invention

The present invention relates to an antiinflammatory and antipyretic cream comprising as an effective component, ketoprofen shown by formula (I).

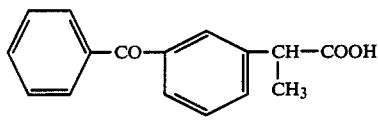

(I)

DEVELOPMENT OF THE INVENTION

Ketoprofen shown by formula (I) above is a nonsteroidal, antiinflammatory and antipyretic drug which exhibits excellent antiinflammatory and antipyretic effect and has been widely used for clinical use. However, side effects such as disturbances of stomach, liver, kidney, etc. have come to problems.

In order to alleviate such side effects, gel ointment of ketoprofen for topical use, cream containing a gelling agent, oleaginous ointment and, emulsion type ointment are disclosed in Japanese Patent Applications under Public Disclosure Nos. 161323/81, 83622,83, 39616/83 and 103311/83, respectively.

Among these compositions for topical use, however, the oleaginous ointments as well as the emulsion type ointments cause crystallization of the effective component either immediately after manufacturing or during storage thereof and as the result, unavoidably involve serious reduction of the antiinflammatory and antipyretic effect because potential crystallization of the effective component is not taken into account in these ointments.

In addition, both the gel ointment for topical use and the cream containing a gelling agent contain lower alcohols such as ethanol as a part of the constituent components; for example, as described in KON-NICHI-NO-HIFU-GAIYOZAI (SKIN TOPICA IN THESE DAYS), pages 241 and 242 (published by Nanzando Publishing Co., Ltd., May 15, 1981), lower alcohols has topically irritating effect and there thus exists a problem on pharmaceutical preparation that they cannot be directly applied to damaged skin areas. For this reason, lower alcohols are extremely unsuited for practical use in the clinical field. Further in any of the topica described above, no specific consideration is given on the stability of ketoprofen which is an effective component in these pharmaceutical preparations.

As a result of extensive investigations with attempts to reduce the side effects of ketoprofen of formula (I) above used for oral administration and to overcome various problems involved in the topica due to factors associated with pharmaceutical preparations, the present inventors have discovered that the ketoprofen-containing cream of the present invention shows an antiinflammatory and antipyretic effect comparable to the pharmaceutical preparation for oral administration, exhibits an excellent effect of permeation and absorption into the skin and, no crystallization occurs with the effective component and the stability of the effective component is excellent. The present inventor has thus accomplished the present invention.

SUMMARY OF THE INVENTION

An object of the present invention is to provide an antiinflammatory and antipyretic cream having minimized side effects and excellent stability.

Another object of the present invention is to provide an antiinflammatory and antipyretic cream which has excellent permeation and absorption into the skin.

The present invention is drawn to the antiinflammatory and antipyretic cream comprising ketoprofen as an effective component and crotamiton as an agent for preventing crystalline precipitation, in a ratio of 0.4 to 1.0 part by weight of crotamiton per 1.0 part by weight of ketoprofen and, a pH range being adjusted to 6.5 to 7.5.

DETAILED DESCRIPTION OF THE INVENTION

The cream of the present invention renders unnecessary to use lower alcohols having skin irritation by formulating into a conventional cream base crotamiton or a specific agent for preventing crystalline precipitation of the effective component. Further the present invention appears to inhibit the crystalline precipitation of the effective component of the cream preparation, thereby resulting in the fact that the cream preparation is characterized by excellent properties.

As will be later shown in Experiments 1, 2 and 3 in which comparison was made between a ketoprofen-containing cream having formulated crotamiton therein and the cream having formulated no crotamiton, crystallization of the effective component was readily noted and reductions in the effect of permeation and absorption into the skin and the antiinflammatory effect were observed, with the latter cream during storage. Further, an optimum ratio of ketoprofen to crotamiton was examined from viewpoints of crystalline precipitation of the effective component and the effect of permeation and absorption into the skin. It has been clarified that the effective component was precipitated out as crystals in the ratio of 6:1 to 3:1 (Experiment 4) and the reduction in the effect of permeation and absorption into the skin was noted in the ratio of 3:4 to 1:2 (Experiment 5). It has thus been discovered that the optimum ratio be in the range of 5:2 to 1:1. Further, an optimum pH range of the preparation was examined from viewpoints of the stability, the effect of permeation and absorption into the skin and the antiinflammatory effect. With pH less than 6.0, the content of ketoprofen decreased during storage (Experiment 6) and, reduction in the effect of permeation and absorption into the skin (Experiment 7) as well as reduction in the antiinflammatory effect (Experiment 8) were noted with pH higher than 8.0. It has thus been discovered that the optimum pH range be 6.5 to 7.5 (inclusive).

The cream of the present invention which has been accomplished based on these facts is a pharmaceutical preparation satisfactorily applicable to practical, clinical use.

The cream of the present invention can be prepared by formulating ketoprofen as an effective component, crotamiton as an agent for preventing crystalline precipitation of the effective component, higher alcohols, oily substances, surfactants, humectants, antiseptic agents, pH controlling agents and water.

Preferred examples of the cream in accordance with the present invention can be embodied by the following processes:

Crotamiton as an agent of preventing crystalline precipitation of the effective component (0.4 to 5.0 wt%: final concentration in the obtained cream; hereafter the same), 1 to 20 wt% of a higher alcohol, 5 to 20 wt% of an oily substance and 1 to 10 wt% of a surfactant are mixed. After melting the resulting mixture, 1.0 to 5.0 wt% of ketoprofen as the effective component is added thereto and the mixture is kept at about 75° C. Separately, 0.01 to 0.5 wt% of a antiseptic agent, 0.1 to 4.5 wt% of a pH controlling agent and 5 to 20 wt% of a humectant are added to 50 to 70 wt% of water. The resulting mixture is dissolved at about 75° C. The solution is added to the melt prepared above followed by emulsification. The emulsion is cooled to prepare a cream having pH of 6.5 to 7.5.

Typical examples of higher alcohols which can be used in preparing the cream of the present invention include cetanol, stearyl alcohol cetostearyl alcohol, 2-octyldodecanol, 2-hexyldecanol, etc. and a mixture thereof.

Preferred examples of oily substances which can be used in the present invention include liquid or solid hydrocarbons such as liquid paraffin, various other paraffins; higher fatty acids such as stearic acid, myristic acid, etc.; higher fatty acid esters such as isopropyl myristate, decyl oleate, etc.; and, methyl polysiloxane, diisopropyl adipate, diethyl sebacate or a mixture thereof.

Preferred examples of surfactants which can be employed in the present invention include sorbitan monooleate, sorbitan sesquioleate, sorbitan trioleate, glyceryl monostearate, polyoxyethylene monostearate, polyoxyethylene monooleate, polyoxyethylene sorbitan monolaurate, polyoxyethylene sorbitan palminate, polyoxyethylene sorbitan monooleate, polyoxyethylene-hardened castor oil, polyoxyethylene cetyl ether, polyoxyethylene stearyl ether polyoxyethylene oleyl ether, polyoxyethylene behenyl ether, polyoxyethylene lanolic alcohol, polyoxyethylene polyoxypropylene cetyl ether, polyoxyethylene nonyl phenyl ether, polyoxyethylene octylphenyl ether, etc. and a mixture thereof.

Preferred examples of humectants which can be used in the present invention include glycerine, propylene glycol, sorbitol, etc.

Preferred examples of antiseptic agents which can be used in the present invention include benzoic acid and its sodium salt, methyl paraben, ethyl paraben, propyl paraben, butyl paraben, sorbitanic acid and its sodium salt, etc. and a mixture thereof.

Preferred examples of pH controlling agents which can be used in the present invention include triethyl amine, triethanolamine, diisopropanolamine, sodium hydroxide, potassium hydroxide, etc.

The ketoprofen-containing cream of the present invention is extremely stable because neither crystal precipitates nor is the content reduced during storage even over a long period of time and at the same time, exhibits excellent permeation and absorption effects with respect to the skin as well as antiinflammatory and antipyretic effect.

Hereafter, the excellent stability and effects achieved by the ketoprofen-containing cream of the present invention are described below in more detail.

COMPARISON IN CRYSTALLINE PRECIPITATION

EXPERIMENT 1

Stability Test:

With the compositions obtained in Examples 1 and 2 and the compositions obtained in Comparison Examples 1 and 2 which contained no agent of preventing crystalline precipitation of the effective component, the presence or absence of crystalline precipitation was observed under respective storage conditions after the preparation. As the storage conditions for the compositions, two conditions of storage at room temperature (11° to 28° C.) and in a refrigerator (4° C.) were chosen.

The results are shown in Table 1 wherein symbols mean:

TABLE 1

| Composition Tested | Test on Stability Condition for Stability | |
|---|---|---|
| | Room Temperature | In Refrigerator |
| Example 1 | — | — |
| Example 2 | — | — |
| Comparison Example 1 | + (15 days) | + (6 days) |
| Comparison Example 2 | + (15 days) | + (4 days) |

In the compositions of Examples 1 and 2, no crystalline precipitation of the effective component and noted under any storage conditions at room temperature and in refrigerator for one month.

EXPERIMENT 2

Test on effect on permeation and absorption in the skin:

After applying the test compositions in Experiment 1, the concentration of the effective component was measured in serum. The run was performed using Wistar male rats weighing 190 to 220 g, 5 per 1 group. Onto the back of each of the aforesaid rats from which hair was removed, 100 mg each of the test compositions (after storage at room temperature for one month after the preparation) was applied at 2 cm×3.5 cm area and blood was collected from the carotid 6 hours after. By liquid chromatography, ketoprofen in serum was quantitatively determined. The results are shown in Table 2.

TABLE 2

| Composition Tested | Test of Effect on Skin Permeation and Absorption Concentration in Serum (μg/ml) |
|---|---|
| Example 1 | 1.18 ± 0.19 |
| Example 2 | 1.15 ± 0.19 |
| Comparison Example 1 | 0.39 ± 0.09 |
| Comparison Example 2 | 0.40 ± 0.07 |

The creams of the present invention showed the effect of permeation and absorption into the skin approximately 3 times greater than that of the creams in which crystalline precipitation was noted.

EXPERIMENT 3

Antiinflammatory Effect:

The antiinflammatory effect of the test compositions in Experiment 1 was determined by an effect on carrageenin induced paw edema. The experiment was performed using 8 Wistar male rats weighing approximately 170 g per one group. After previously measuring the volume of left hind paw, 50 mg each of the test compositions (stored at room temperature for one month after the preparation) was applied twice, left hind paw of the rat, 2 hours and 1 hour before injection of an inflammatory agent. As the inflammatory agent, 0.1 ml of a 1% carrageenin solution was subcutaneously injected at the left hind paw. The volume of the left hind paw was measured 3 hours after and a swelling was determined based on the volume before injecting the inflammatory agent. A group in which no test composition was applied was made a control group and the inhibition rate was calculated based thereon as follows. The results are shown in Table 3.

Inhibition Rate (%) =

$$\frac{\text{Rate of swelling in Control Group} - \text{Rate of swelling in Group Given Test Preparation}}{\text{Rate of Swellling in Control Group}} \times 100$$

TABLE 3

Effect on carrageenin induced paw edema

| Preparation Tested | Inhibition Rate (%) | Potency Ratio*[1] |
|---|---|---|
| Example 1 | 39.4 | 0.86 |
| Example 2 | 37.8 | 0.82 |
| Comparison Example 1 | 12.1 | 0.26 |
| Comparison Example 2 | 11.4 | 0.25 |
| Oral Administration*[2] | 45.9 | 1.00 |

*[1]The inhibition rate in oral administration was made a potency of 1.00
*[2]5 mg/kg, Folia Pharmacologica Japonica vol. 70, page 543 (1974)

The creams of the present invention possess the antiinflammatory effect approximately 3 times greater than that of the compositions in which crystalline precipitation was noted. The antiinflammatory effect of the creams of the present invention is comparable to the effect obtained by oral administration in a dose of 5 mg/kg.

As shown above, the creams of the present invention which contain the agent of preventing crystalline precipitation of the effective component exhibit excellent effects without causing crystalline precipitation, as demonstrated in Experiments 1, 2 and 3.

EXAMINATION ON RATIO OF KETOPROFEN TO CROTAMITON

EXPERIMENT 4

Stability Test:

The quantity of crotamiton was varied from the formulations of Example 1. By controlling the variant with water, compositions having various ratios of ketoprofen to crotamiton ranging from 6:1 to 1:2 were prepared. After preparing these compositions, the presence or absence of crystalline precipitation of the effective component was observed under respective storage conditions. The storage conditions of the compositions were the same as in Experiment 1. The results are shown in Table 4.

TABLE 4

Test on Stability

| Amount of Crotamiton per 3 g of Ketoprofen | Condition for Storage | |
|---|---|---|
| | Room Temperature | Refrigerator |
| 0.5 g (6:1) | + (10 days) | + (4 days) |
| 1 g (3:1) | + (18 days) | + (8 days) |
| 1.2 g (5:2) | — | — |
| 2 g (3:2) | — | — |
| 3 g (1:1) | — | — |
| 4 g (3:4) | — | — |
| 6 g (1:2) | — | — |

( ): Ratio of ketoprofen to crotamiton
+: Crystallization occurred.
—: No crystallization occurred.
(day): Passage time until crystal was precipitated.

The compositions having the ketoprofen-to-crotamiton ratio of 5:2 to 1:2 caused no crystalline precipitation of the effective component under storage conditions either at room temperature or in refrigerator for one month.

EXPERIMENT 5

Test on Effect of Permeation and Absorption in the Skin:

With the compositions having the ketoprofen-to-crotamiton ratio of 5:2 to 1:2 out of the compositions in Experiment 4, the effect of permeation and absorption of the effective component into the skin was determined in a manner similar to Experiment 2. The results are shown in Table 5.

TABLE 5

Test of Effect on Skin Permeation and Absorption

| Ratio of Ketoprofen to Crotamiton | Concentration in Serum (μg/ml) |
|---|---|
| 5:2 | 1.14 ± 0.22 |
| 3:2 | 1.12 ± 0.18 |
| 1:1 | 0.86 ± 0.14 |
| 3:4 | 0.51 ± 0.12 |
| 1:2 | 0.46 ± 0.09 |

In the compositions having the ketoprofen-to-crotamiton ratio of 5:2 to 1:1, no reduction in the effect of permeation and absorption into the skin was noted.

COMPARISON IN PH VARIATION

EXPERIMENT 6

Stability Test:

Creams having pH ranging from 4.0 to 8.0 were prepared by modifying the amount of triethanolamine as a pH controlling agent in the compositions of Examples 1. With these creams, the change in the content of the effective component was examined by liquid chromatography after 1 month lapsed under the storage condition at 50° C. after the preparation. The results are shown in Table 6 wherein the numerals found in "Content" represent percentage determined when the starting point was made 100%.

TABLE 6

Test on Stability

| pH in Composition Tested | Content (%) |
|---|---|
| 4.0 | 75 |
| 5.0 | 82 |
| 6.0 | 90 |

TABLE 6-continued

| Test on Stability | |
|---|---|
| pH in Composition Tested | Content (%) |
| 6.5 | 100 |
| 6.8 | 101 |
| 7.2 | 101 |
| 7.5 | 101 |
| 8.0 | 101 |

As is noted from the results above, no reduction in the content of the effective component was noted with pH of 6.5 to 8.0 but stable.

EXPERIMENT 7

Test on effect of Permeation and Absorption into the Skin:

With the test compositions showing pH 6.5 to 8.0 out of the compositions of Experiment 6, the effect of permeation and absorption of the effective component into the skin was measured in a manner similar to Experiment 2. The results are shown in Table 7.

TABLE 7

| Test of Effect on Skin Permeation and Absorption | |
|---|---|
| pH in Test Composition | Concentration in Serum (μg/ml) |
| 6.5 | 1.12 ± 0.25 |
| 6.8 | 1.06 ± 0.13 |
| 7.2 | 1.06 ± 0.11 |
| 7.5 | 0.81 ± 0.11 |
| 8.0 | 0.47 ± 0.08 |

In the creams of the present invention, the effect of permeation and absorption into the skin somewhat decreased from pH of 7.5 and considerably decreased at pH of 8.0.

EXPERIMENT 8

Antiinfammatory Effect:

The antiinfammatory effect was examined with the test compositions of Experiment 7, in a manner similar to Experiment 3. The results are shown in Table 8.

TABLE 8

| Effect on carrageenin induced paw edema | | |
|---|---|---|
| pH of Test Composition | Inhibition Rate (%) | Potency Ratio*[1] |
| 6.5 | 3.96 | 1.74 |
| 6.8 | 40.2 | 1.76 |
| 7.2 | 38.3 | 1.68 |
| 7.5 | 36.2 | 1.59 |
| 8.0 | 25.1 | 1.10 |
| Reference Example 1 (Indomethacin gel ointment) | 22.8 | 1.00 |

*[1]The prevention rate in Reference Example 1 was made potency ratio of 1.00.

The creams having pH ranging from 6.5 to 7.5 showed the antiinflammatory effect approximately 1.7 time greater than that of indomethacine gel ointment.

As demonstrated above, the cream of the present invention is characterized in that:

(1) The optimum ratio of ketoprofen to crotamiton ranges from 5:2 to 1:1, as shown in Experiments 4 and 5;

(2) The optimum pH range is between 6.5 and 7.5 (inclusive), as shown in Experiments 6, 7 and 8.

Hereafter, the present invention will be described in detail with reference to the following examples but is not deemed to be limited only thereto.

EXAMPLE 1

A mixture of 2 g of crotamiton, 5 g of liquid paraffin, 5 g of white petrolatum, 10 g of stearyl alcohol, 4 g of polyoxyethylene monostearate, 4 g of glyceryl monostearate and 0.3 g of methyl polysiloxane melted and 3 g of ketoprofen was added to the melt. The resulting mixture was kept at a temperature of about 75° C.

Separately, 0.1 g of methyl parahydroxybenzoate, 0.02 g ofpropyl parahydroxybenzoate, 1.5 g of triethanolamine and 6 g of glycerine were dissolved in 59.08 g of purified water at a temperature of about 75° C. The solution was added to the mixture previously prepared and the mixture was emulsified. After cooling the emulsion to congeal, a cream for topical use was obtained. The pH of the cream was 6.5.

EXAMPLE 2

A mixture of 2 g of crotamiton, 5 g of liquid paraffin, 5 g of white petrolatum, 10 g of stearyl alcohol, 4 g of polyoxyethylene monostearate, 4 g of glyceryl monostearate and 0.3 g of methyl polysiloxane melted and 3 g of ketoprofen was added to the melt. The resulting mixture was kept at a temperature of about 75° C.

Separately, 0.1 g of methyl parahydroxybenzoate, 0.02 g of propyl parahydroxybenzoate, 0.5 g of potassium hydroxide and 6 g of glycerine were dissolved in 60.08 g of purified water at a temperature of about 75° C. The solution was added to the mixture previously prepared and the mixture was emulsified. After cooling the emulsion to congeal, a cream for topical use was obtained. The pH of the cream was 6.5.

EXAMPLE 3

A mixture of 2 g of crotamiton, 7 g of white petrolatum, 8 g of stearyl alcohol, 10 g of isopropyl myristate, 3 g of 2-octyldodecanol, 4 g of polyoxyethylene monostearate, 4 g of glyceryl monostearate and 0.3 g of methyl polysiloxane melted and 3 g of ketoprofen was added to the melt. The resulting mixture was kept at a temperature of about 75° C.

Separately, 0.1 g of methyl parahydroxybenzoate, 0.02 g of propyl parahydroxybenzoate, 2 g of triethanolamine and 6 g of glycerine were dissolved in 59.08 g of purified water at a temperature of about 75° C. The solution was added to the mixture previously prepared and the mixture was emulsified. After cooling the emulsion to congeal, a cream for topical use was obtained. The pH of the cream was 7.3.

Creams were prepared in the manner of Example 1 to obtain the creams having compositions of Examples 4 through 8 shown below.

EXAMPLE 4

| | |
|---|---|
| Ketoprofen | 1 g |
| Crotamiton | 1 g |
| Liquid paraffin | 5 g |
| White petrolatum | 5 g |
| Stearyl alcohol | 10 g |
| Polyoxyethylene monostearate | 4 g |
| Glyceryl monostearate | 4 g |
| Methyl polysiloxane | 0.3 g |
| Methyl parahydroxybenzoate | 0.1 g |
| Propyl parahydroxybenzoate | 0.02 g |

-continued

| | |
|---|---|
| Triethanolamine | 0.7 g |
| Glycerine | 6 g |
| Purified water | 62.88 g |
| pH | 7.4 |

EXAMPLE 5

| | |
|---|---|
| Ketoprofen | 2 g |
| Crotamiton | 2 g |
| Liquid paraffin | 5 g |
| White petrolatum | 5 g |
| Stearyl alcohol | 10 g |
| Polyoxyethylene monostearate | 4 g |
| Glyceryl monostearate | 4 g |
| Methyl polysiloxane | 0.3 g |
| Methyl parahydroxybenzoate | 0.1 g |
| Propyl parahydroxybenzoate | 0.02 g |
| Triethanolamine | 1.3 g |
| Glycerine | 6 g |
| Purified water | 60.28 g |
| pH | 7.2 |

EXAMPLE 6

| | |
|---|---|
| Ketoprofen | 3 g |
| Crotamiton | 2 g |
| Liquid paraffin | 5 g |
| White petrolatum | 5 g |
| Stearyl alcohol | 10 g |
| Polyoxyethylene monostearate | 4 g |
| Glyceryl monostearate | 4 g |
| Methyl polysiloxane | 0.3 g |
| Methyl parahydroxybenzoate | 0.1 g |
| Propyl parahydroxybenzoate | 0.02 g |
| Triethanolamine | 2 g |
| Glycerine | 6 g |
| Purified water | 58.58 g |
| pH | 7.2 |

EXAMPLE 7

| | |
|---|---|
| Ketoprofen | 4 g |
| Crotamiton | 2 g |
| Liquid paraffin | 5 g |
| White petrolatum | 5 g |
| Stearyl alcohol | 10 g |
| Polyoxyethylene monostearate | 4 g |
| Glyceryl monostearate | 4 g |
| Methyl polysiloxane | 0.3 g |
| Methyl parahydroxybenzoate | 0.1 g |
| Propyl parahydroxybenzoate | 0.02 g |
| Triethanolamine | 2.6 g |
| Glycerine | 6 g |
| Purified water | 56.98 g |
| pH | 7.2 |

EXAMPLE 8

| | |
|---|---|
| Ketoprofen | 5 g |
| Crotamiton | 2 g |
| Liquid paraffin | 5 g |
| White petrolatum | 5 g |
| Stearyl alcohol | 10 g |
| Polyoxyethylene monostearate | 4 g |
| Glyceryl monostearate | 4 g |
| Methyl polysiloxane | 0.3 g |
| Methyl parahydroxybenzoate | 0.1 g |
| Propyl parahydroxybenzoate | 0.02 g |
| Triethanolamine | 3.2 g |
| Glycerine | 6 g |
| Purified water | 55.38 g |
| pH | 7.2 |

Comparison examples and reference example shown below are creams used for purposes of comparing with the creams of the present invention in the experiments hereinbefore.

COMPARISON EXAMPLE 1

A cream containing 3% of ketoprofen prepared in a manner similar to Example 1 except that crotamiton as an agent for preventing crystalline precipitation of the effective component was omitted from the composition of Example 1.

COMPARISON EXAMPLE 2

A cream containing 3% of ketoprofen prepared in a manner similar to Example 2 except that crotamiton as an agent for preventing crystalline precipitation of the effective component was omitted from the composition of Example 2.

REFERENCE EXAMPLE 1

Commercially available gel ointment containing indomethacin.

While the invention has been described in detail and with reference to specific embodiments thereof, it will be apparent to one skilled in the art that various changes and modifications can be made therein without departing from the spirit and scope thereof.

What is claimed is:

1. An antiinflammatory and antipyretic cream comprising ketoprofen and crotamiton as an agent for preventing crystalline precipitation,
   crotamiton being in a ratio of 0.4 to 1.0 part by weight per 1.0 part by weight of ketoprofen; and;
   a pH range of said cream being adjusted to 6.5 to 7.5.
2. The antiinflammatory and antipyretic cream of claim 1 which contains 1.0 to 5.0 wt% of ketoprofen and 0.4 to 5.0 wt% of crotamiton and, further containing 1 to 20 wt% of a higher alcohol, 5 to 20 wt% of an oily substance, 1.0 to 10.0 wt% of a surfactant, 5 to 20 wt% of a humectant, 0.01 to 0.5 wt% of a antiseptic agent, 0.1 to 4.5 wt% of a pH controlling agent and 50 to 70 wt% of water.

* * * * *

UNITED STATES PATENT AND TRADEMARK OFFICE
CERTIFICATE OF CORRECTION

PATENT NO. : 4,534,980

DATED : August 13, 1985

INVENTOR(S) : Yasuo Itoh, Hideo Kato, Kugako Matsumura, Tomoyasu Nishikawa, Akira Hisano, Takehisa Yamada and Eiichi Koshinaka It is certified that error appears in the above-identified patent and that said Letters Patent is hereby corrected as shown below:

Col. 1, line 30; "83622,83," should read -- 83622/83, --

Col. 4, line 18; insert before "TABLE 1" the paragraph

-- -: No crystalline precipitation of the effective component was noted.

+: Crystalline precipitation of the effective component was noted.

( ): Elapse of time (day) until the effective component precipitated as crystals. --

Col. 6, line 54; "Examples" should read -- Example --
Col. 7, line 41; "Antiinfammatory" should read -- Antiinflammatory --
Col. 7, line 42; "antiinfammatory" should read -- antiinflammatory --
Col. 8, line 13; "ofpropyl" should read -- of propyl --

Signed and Sealed this

Twenty-sixth Day of November 1985

[SEAL]

Attest:

DONALD J. QUIGG

Attesting Officer

Commissioner of Patents and Trademarks